(12) United States Patent
Bismuth et al.

(10) Patent No.: US 10,314,665 B2
(45) Date of Patent: Jun. 11, 2019

(54) METHOD FOR MEDICAL IMAGE PROCESSING

(71) Applicant: GENERAL ELECTRIC COMPANY, Schenectady, NY (US)

(72) Inventors: Vincent Bismuth, Buc (FR); Régis Vaillant, Buc (FR); Sébastien Gorges, Buc (FR); Maxime Cazalas, Buc (FR); Liliane Ramus, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 60 days.

(21) Appl. No.: 15/108,032

(22) PCT Filed: Sep. 10, 2014

(86) PCT No.: PCT/US2014/054979
§ 371 (c)(1),
(2) Date: Jun. 24, 2016

(87) PCT Pub. No.: WO2015/099843
PCT Pub. Date: Jul. 2, 2015

(65) Prior Publication Data
US 2016/0317245 A1 Nov. 3, 2016

(30) Foreign Application Priority Data
Dec. 24, 2013 (FR) ...................... 13 63558

(51) Int. Cl.
*G06F 3/01* (2006.01)
*A61B 90/00* (2016.01)
(Continued)

(52) U.S. Cl.
CPC ............ *A61B 90/361* (2016.02); *A61B 34/25* (2016.02); *A61B 90/37* (2016.02); *G06F 3/013* (2013.01);
(Continued)

(58) Field of Classification Search
CPC .................................... G06T 3/40; G06F 3/01
See application file for complete search history.

(56) References Cited

U.S. PATENT DOCUMENTS 4,950,069 A * 8/1990 Hutchinson ............ A61B 3/113
351/210
6,711,433 B1 3/2004 Geiger et al.
(Continued)

FOREIGN PATENT DOCUMENTS

JP 2007/319327 * 12/2007 ............... G06T 1/00

OTHER PUBLICATIONS

International Search Report and Written Opinion for PCT/US2014/054979, dated Nov. 10, 2014, 8 pages.
(Continued)

*Primary Examiner* — Olga V Merkoulova

(57) ABSTRACT

An image processing method applied by a medical imaging device is proposed, including at least one camera and at least one display screen on which is displayed a medical image showing a region of interest of a patient, the method being characterized in that the region of interest is determined by the following steps, the screen and the camera being laid out so as to be facing a practitioner simultaneously, acquisition by the camera of at least one tracking image containing the eyes of the practitioner, analysis of the tracking image so as to localize in the medical image at least one pixel of interest contemplated by the practitioner on the screen from the orientation of the eyes of the practitioner, processing the medical image so as to select the region of interest from the localized pixel of interest.

9 Claims, 5 Drawing Sheets

(51) Int. Cl.
*A61B 34/00* (2016.01)
*G06T 3/40* (2006.01)
*G06T 5/00* (2006.01)
*G06T 7/00* (2017.01)
*G06T 7/73* (2017.01)
*A61B 17/00* (2006.01)

(52) U.S. Cl.
CPC ............ *G06T 3/4038* (2013.01); *G06T 5/008* (2013.01); *G06T 7/0012* (2013.01); *G06T 7/74* (2017.01); *A61B 2017/00216* (2013.01); *G06T 2200/32* (2013.01); *G06T 2207/20104* (2013.01); *G06T 2207/20208* (2013.01); *G06T 2207/20221* (2013.01); *G06T 2207/30201* (2013.01)

(56) References Cited

U.S. PATENT DOCUMENTS

| | | | |
|---|---|---|---|
| 2003/0113003 A1* | 6/2003 | Cline | G06T 7/0012 382/128 |
| 2003/0214710 A1* | 11/2003 | Takahashi | G02B 27/225 359/443 |
| 2006/0082542 A1* | 4/2006 | Morita | A61B 5/7475 345/156 |
| 2006/0109237 A1* | 5/2006 | Morita | G06F 3/013 345/156 |
| 2006/0109238 A1* | 5/2006 | Lau | G06F 3/013 345/156 |
| 2006/0139319 A1* | 6/2006 | Kariathungal | G06F 3/013 345/156 |
| 2007/0230666 A1 | 2/2007 | Yokokawa et al. | |
| 2011/0060423 A1 | 3/2011 | Bonfiglio et al. | |
| 2011/0251483 A1 | 10/2011 | Razzaque et al. | |
| 2012/0235064 A1 | 9/2012 | Guez | |
| 2013/0030571 A1 | 1/2013 | Ruiz Morales et al. | |
| 2014/0321710 A1* | 10/2014 | Robert | A61B 6/12 382/103 |

OTHER PUBLICATIONS

Ohno et al., "FreeGaze: A Gaze Tracking System for Everyday Gaze Interaction," NTT Communication Science Laboratories, NTT Corporation, pp. 125-132, 2002.

* cited by examiner

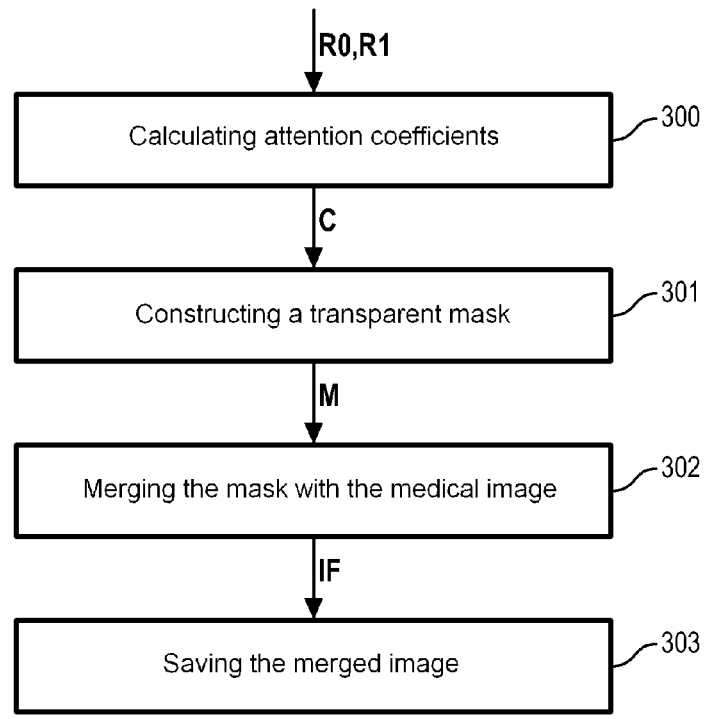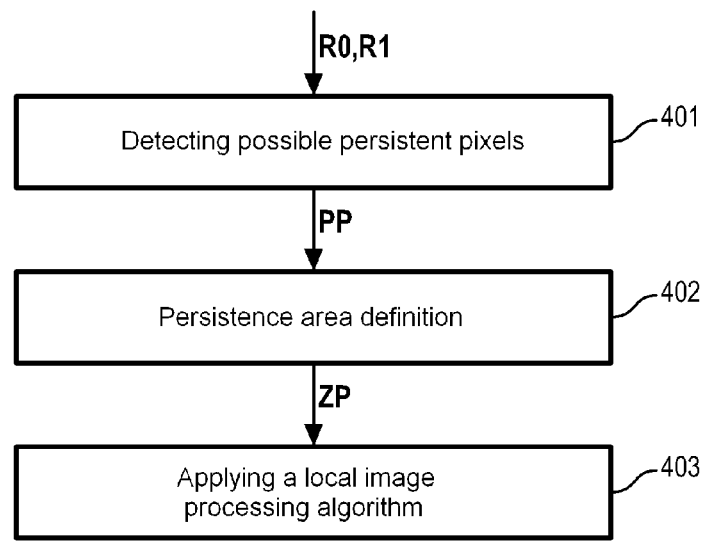

Gaze tracking  Collimation/attenuation  Image processing

Quantification

METHOD FOR MEDICAL IMAGE PROCESSING

CROSS-REFERENCE TO RELATED APPLICATIONS

This application is a filing under 35 U.S.C. 371 of copending international application number PCT/US2014/054979, filed Sep. 10, 2014, which claims priority to French application number 1363558, filed Dec. 24, 2013; both of said applications are incorporated herein by reference in their entireties.

TECHNICAL FIELD

Embodiments of the invention relate to the field of medical imaging devices and to that of image processing methods allowing an improvement in the ergonomics of such devices.

STATE OF THE ART

The use of imaging devices has become more democratic in the medical field, notably within the scope of interventional radiology.

Medical imaging devices comprise a display screen for viewing an image containing a portion of the body of a patient, and at least one input peripheral intended to be manipulated by a practitioner for selecting an area of interest of the patient, viewed on the screen, or for starting applications requiring interaction with the image such as clicks on particular locations (a mouse, a keyboard, or the actual screen if the latter comprises a touchpad).

However, these input peripherals are not always practical for use, and their use may interrupt the concentration of the practitioner.

Such an interruption in concentration extends the duration of use of the imaging device, and therefore the total duration of a medical intervention in progress made by the practitioner.

Further, such an interruption in concentration may be a problem in the case when the imaging device is used while the practitioner is operating on a patient. Indeed, the practitioner thus has to let hold of surgical instruments which he/she holds in his/her hands, grasp an input peripheral, select an area of interest in the image displayed on the screen, release the input peripheral in order to pick up again the surgical instruments with his/her hands with view to continuing the operation.

In interventional imaging, as the hands of the practitioner are occupied with medical tools which he/she manipulates, the input peripherals cannot be used while the imaging device acquires images.

Further, the imaging systems do not traditionally have access to the information indicating what is of interest for the physician, in particular in each of the acquired images or reviewed. This limits the display optimizations which may result from this.

BRIEF DESCRIPTION OF THE INVENTION

An object of the invention is, therefore, to reduce the number of manipulations to be made by a practitioner for selecting a region of interest in an image displayed on a medical imaging device.

For this purpose, an imaging processing method is proposed, applied by a medical imaging device comprising at least one camera and at least one display screen on which a medical image showing a region of interest of a patient is displayed, the method being characterized in that the region of interest is determined by the following steps, the screen and the camera being laid out so as to be facing a practitioner simultaneously: acquiring through the camera at least one tracking image containing the eyes of the practitioner, analyzing the tracking image so as to localize in the medical image at least one pixel of interest contemplated by the practitioner on the screen from the orientation of the eyes of the practitioner, and processing the medical image so as to select the region of interest from the localized pixel of interest.

By means of this method, the region of interest may be automatically determined, without requiring any input peripheral or breaking the concentration of the practitioner.

Embodiments of the invention may also be completed by the following features, taken alone or in any of their technically possible combinations.

An embodiment of the method may comprise a step for displaying on the screen a pattern localizing the determined region of interest in the displayed medical image. This allows collaborators of the practitioner to understand where the region estimated as interesting by the practitioner in the image is located, without the latter having to use any pointing device.

An embodiment of the method may also comprise a step for determining and displaying descriptive information of the determined region of interest.

An embodiment of the method may also comprise a step for adjusting the contrast and/or the luminosity of at least one portion of the medical image so as to highlight the determined region of interest relatively to the remainder of the displayed medical image. This gives the possibility of focusing the attention of the practitioner and of possible collaborators without overloading the displayed medical image.

An embodiment of the method may also comprise a step during which the displayed image is zoomed as a whole, or only in a portion of this image including the area of interest. By zoom is meant here the application of a magnification factor over all or part of the image.

An embodiment of the method may be repeated for a plurality of medical images successively displayed on the screen, and comprising the steps of: storing in memory a plurality of determined regions of interest for the plurality of displayed medical images, detecting at least one persistent pixel comprised in each region of interest of said plurality, and applying a local processing algorithm achieved in at least one following medical image, the realtime processing algorithm being restricted to a portion of the following medical image containing the persistent pixel.

Embodiments of the invention allow for the detection of areas which have been examined for a long time by the practitioner, and automatic triggering of the local processing algorithm. Moreover, as this processing is confined to a portion of the medical image, it consumes less memory and execution time resources when it is applied by an image processing module.

The imaging processing method may further comprise the following steps, after acquiring and analyzing a plurality of tracking images: determining for each pixel of the medical image, a respective attention coefficient depending on the number of tracking images in which the pixel has crossed the gaze of the practitioner, constructing a mask of transparent pixels, each transparent pixel corresponding to a respective attention coefficient, merging the medical image and the mask into an attention image allowing viewing of the mask and of the medical image by transparence through the mask, and saving the attention image in a storage unit of the medical imaging device.

The attention image may then be consulted by the practitioner or collaborators for diagnosing or teaching purposes.

The method may also comprise the activation of a light source of the medical imaging device, if the analysis step fails in localizing any pixel of interest contemplated by the practitioner on the screen, from at least one acquired tracking image. For example, the light source may be oriented towards an operation area by the practitioner.

A medical imaging device is also proposed, comprising at least one display screen, at least one camera, and an image processing module, the device being characterized in that the display screen and the screen are laid out so as to be facing a practitioner simultaneously, and in that the image processing module is adapted for: localizing in a medical image displayed by the screen at least one pixel of interest contemplated by the observer from the orientation of the eyes of the practitioner, displayed in a tracking image acquired by the camera, and for selecting in the medical image, a region of interest from the localized pixel of interest.

DESCRIPTION OF THE FIGURES

Other features, objects and advantages of the invention will become apparent from the following description, which is purely illustrative and nonlimiting and which should be read with reference to the appended drawings wherein:

FIGS. 4 and 5 are flowcharts of sub-steps of an analysis step illustrated in FIG. 3;

In the whole of the figures, similar elements bear the same references.

DETAILED DESCRIPTION OF THE INVENTION

Medical Imaging Device

Figure 1:
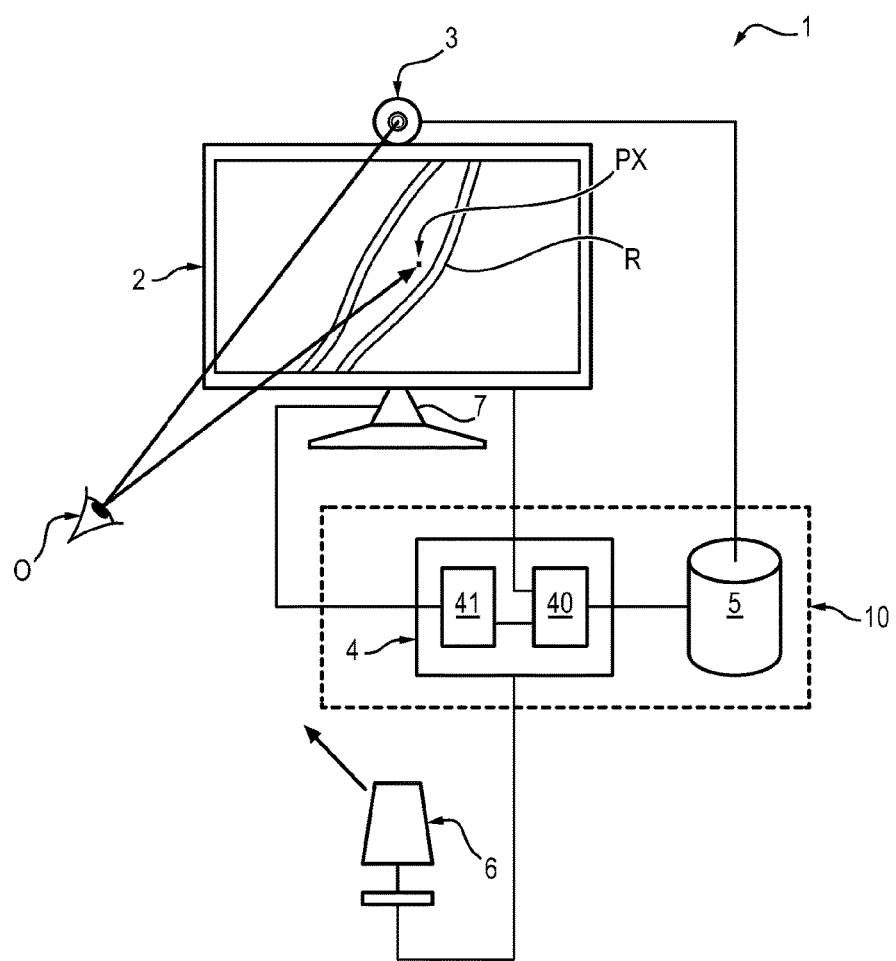
FIG. 1 schematically illustrates a medical imaging device according to an embodiment of the invention.

With reference to FIG. 1, a medical imaging device 1 comprises a display screen 2, a camera 3, an image processing module 4 and a data storage module 5.

The screen 2 and the camera 3 are laid out so as to be facing a practitioner 0 simultaneously (one eye of whom is schematically illustrated in FIG. 1). The camera 3 may be positioned fixedly relatively to the screen 3, for example above an upper edge of the screen 1.

The screen 2 is connected to the image processing module 4 and is adapted for displaying images stemming from this image processing module 4.

The camera 3 is adapted for acquiring images and transferring them to the image processing module 4.

The image processing module 4 typically comprises at least one processor 40 suitable for applying a gaze tracking algorithm, and at least one memory unit 41 suitable for storing in memory, images to be processed by the processor 40 or already processed by the processor 41, for example a RAM memory.

The image processing module 4 is moreover configured so as to provide read and write access to the storage module 5, which may for example comprise one or several memories of the flash, EEPROM, hard disc, SSD type, etc.

The image processing module 4 and the storage module 5 may be grouped together within a same computing device 10, for example a computer.

Medical Imaging Method

Figure 2:
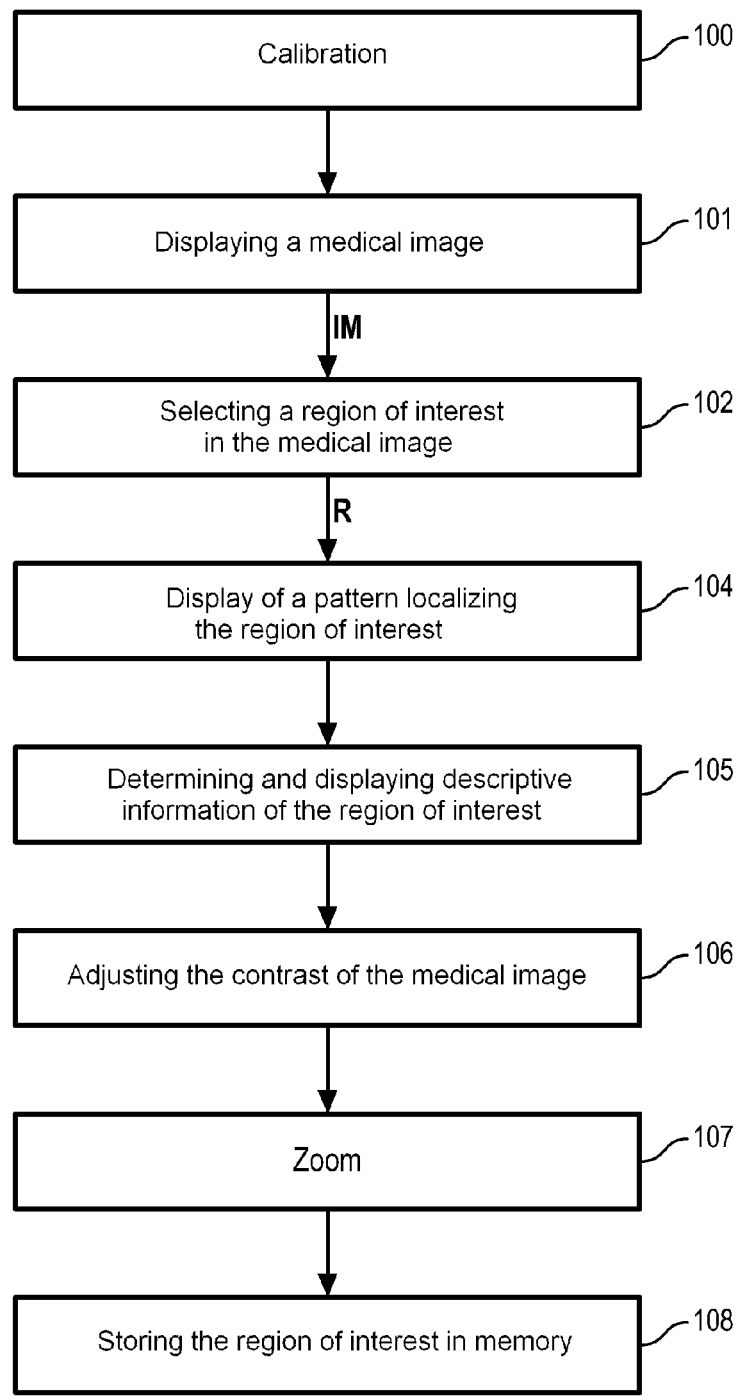
FIG. 2 is a flowchart of steps of an image processing method applied by the device illustrated in FIG. 1.

With reference to FIG. 2, an image processing method applied by the medical imaging device 1 comprises the following steps, while a practitioner is facing the screen 2 and the camera 3 simultaneously.

In a preliminary calibration step 100, a plurality of reference images is acquired by camera 2 and transferred to the imaging processing module 3, which determines reference data allowing configuration of the practitioner's gaze tracking algorithm relatively to the dimensions of the screen 2; these reference data are then saved in the storage module 5. This calibration 100 typically comprises one or several correlations between orientations of the eyes of the practitioner and reference positions on the screen.

In a step 101, a medical image IM, i.e. an image showing contents with a medical nature, is displayed on the screen 2. This medical image IM may be read from the storage module 5, or else stem from an image acquisition device (not illustrated) oriented towards a portion of the body of a patient, subject of a medical intervention ensured by the practitioner (for example an X-ray image acquisition device).

In a selection step 102, at least one region of interest is displayed in the displayed image, for example a vessel of the patient.

Figure 3:
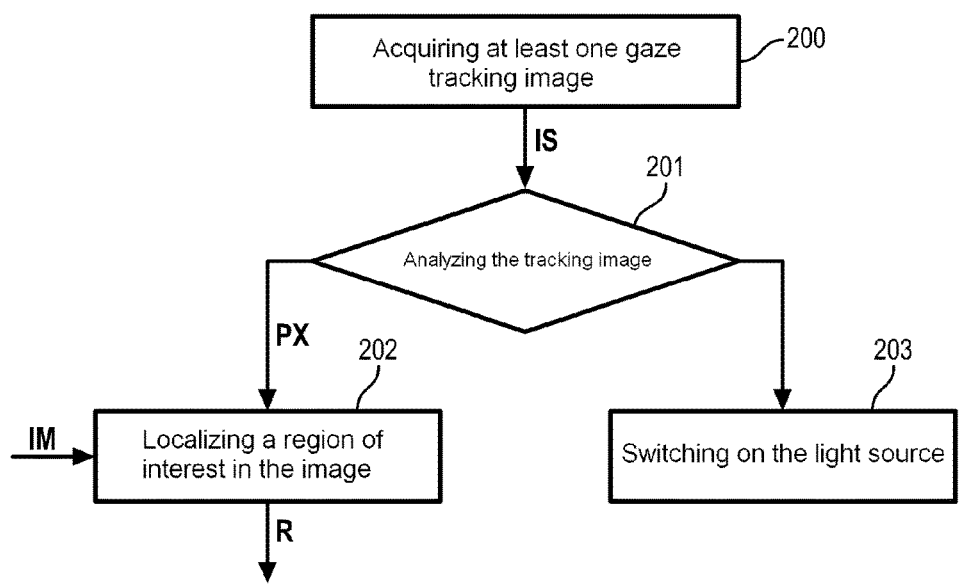
FIG. 3 is a sub-step flowchart of a step for selecting a region of interest illustrated in FIG. 2.

With reference to FIG. 3, this selection step 102 comprises the following sub-steps.

In a sub-step 200, at least one tracking image IS is acquired by the camera oriented towards the practitioner. This tracking image IS may either show the eyes of the practitioner or not; moreover, the eyes of the practitioner, if they are shown in the tracking image IS, may be oriented towards an area of the screen 2, or else towards an area located outside the screen 2.

In a sub-step 201, the tracking image IS is passed on to the image processing module 4, which then inspects the contents of the tracking image IS, and more specifically the orientation of the eyes of the practitioner possibly present in the tracking image IS. This step 201 may typically apply a pattern recognition algorithm, adapted for detecting eyes and for detecting the orientation of the axis of the gaze of the practitioner by analyzing, for each of the two eyes, the position of each iris in space (for example the recognition algorithm detailed in the article entitled "FreeGaze: A Gaze Tracking System for Everyday Gaze Interaction", by Takehiko Ohno, Naoki Mukawa and Atsushi Yoshikawa).

If the axis of the gaze of the practitioner crosses the screen 2 in a target area, then the analysis step 201 determines at least one pixel of interest PX of the screen 2 comprised in this target area. This determination is typically carried out by means of the reference data recorded in the storage module 5 during the calibration step 100.

In a step 203, the image processing module 4 determines, from the pixel(s) of interest of screen 2, and the displayed medical image IM, a region of interest R comprised in the medical image IM. This region of interest may typically be determined by segmentation of the medical image IM into several objects, and then selecting an object close to or comprising the determined pixel of interest PX.

The region of interest R may be determined from a reference pixel, or else from several pixels of interest determined in the same tracking image IS or else in a plurality of tracking images successively acquired by the camera 3.

Returning to FIG. 2, the determined region of interest R may be utilized in several ways.

In a step 104, a pattern corresponding to the region of interest may be determined and displayed on the screen in the medical image IM, such as a cursor pointing to the pixel of interest PX or a closed line delimiting the region of interest R.

The thereby displayed pattern gives the possibility to other persons (colleagues, auxiliaries, medical personnel, etc.) of tracking on the screen 2, the gaze of the practitioner 0, whether this is when the latter performs an intervention on the patient concerned by the images displayed on the screen 2, or else when comments are made on the course of a past intervention. Auxiliaries of the practitioner seeing that the practitioner has focused his/her attention on a particular area of the body of a patient, may for example anticipate the preparation of surgical instruments which the practitioner would possibly need for treating this area.

In a step 105, descriptive information of the region of interest R may also be displayed on the screen 2, for example as an overprinting of the medical image IM. This descriptive information may for example be visual marks, numerical values and/or text, for example the diameter of a vein).

In a step 106, the contrast and/or the luminosity of all or part of the image IM displayed on screen 2 may be adjusted so as to highlight the selected region of interest. For example provision may be made for increasing the luminosity of the pixels of the image IM contained in the region of interest R, and for reducing the luminosity of the other pixels of the image IM. Preferably, the luminosity of the other pixels of the image is not reduced to zero so as to be able to distinguish the objects which they represent.

In a step 107, all or part of the image IM displayed on screen 2 is zoomed so as to focus the attention of the observer on the region of interest. For example limitation of the zoom to a portion of the image IM which follows the gaze of the observer may be provided, so as to provide a magnifying glass effect at the region of interest.

In a step 108, the region of interest R is stored in memory in the memory unit 41 or in the storage module 5.

Steps 103 to 108 may be applied sequentially, in any order or else in parallel.

The preceding steps may moreover be repeated for a plurality of medical images successively displayed on the screen 2. If the acquisition frequency of the camera 3 is greater than the displayed frequency of the screen 2, several tracking images may be acquired by the camera 3 for a same medical image IM displayed on the screen 2. For example provision may be made for having both of these frequencies identical, so as to acquire a tracking image IS for each image displayed on the screen 2.

With reference to FIG. 4, the method may comprise a step 300 for calculating attention coefficients C, this step 300 being carried out after the selection step 102 has been applied several times, for a plurality of medical images, thereby elaborating a plurality of regions of interest R0, R1. Each attention coefficient C is assigned to a respective pixel of a current medical image IM and depends on the number of regions of interest associated with said plurality of previous medical images in which the pixel is included. For example, an attention coefficient equal to zero may mean that the corresponding pixel is comprised in N regions of interest, each region of interest being selected for a respective medical image IM. Each coefficient C may be calculated from a predetermined number of previous medical images successively displayed on the screen 2.

In a step 301, a mask M of transparent pixels is constructed from the determined attention coefficients. The transparent mask M is a set of transparent pixels with dimensions at most equal to the dimensions of the medical image IM.

In a step 302, the mask M of transparent pixels and the current medical image are merged into a same image, a socalled attention image. In this attention image, the transparent mask M is in the foreground, while the medical image is in the background.

In a step 303, the thereby obtained attention image IF is then stored in memory in the storage module 5 of the medical imaging device 1.

Several attention images IF may be successively stored in memory in the storage module 5, for example in a video format, so as to be able to be read by a suitable reader, in order to analyze how the practitioner has used the screen during his/her intervention.

Moreover, from a plurality of regions of interest R0, R1 stored in memory during step 105, persistent areas on screen 3 may be determined for applying the following steps (FIG. 5).

In a step 401, the image processing module 4 checks whether there exists a pixel of the screen 2 comprised in a predetermined number of successive regions of interest R0, R1 stored in memory in the storage module 5, this number being greater than or equal to two. If such a persistent pixel PP exists, this means that the practitioner has examined for a relatively long time a same portion of the medical image IM displayed on the screen 2.

In a step 402, a persistent area ZP is defined by the image processing module 4 from the persistent pixel PP. The persistent area may be of a predetermined shape, for example a rectangle or a circle centered on the detected persistent pixel, and with dimensions determined according to the size in pixels of the image IM.

In a step 403, an algorithm for processing local images is applied, i.e. restricted to the defined persistent area. This step 403 is particularly advantageous when the local image processing algorithm is particularly costly in terms of memory and of execution rapidity. Indeed, by restricting the number of pixels processed by such an algorithm, it is possible to save on memory resources and on processor time for applying such an algorithm.

Figure 6:
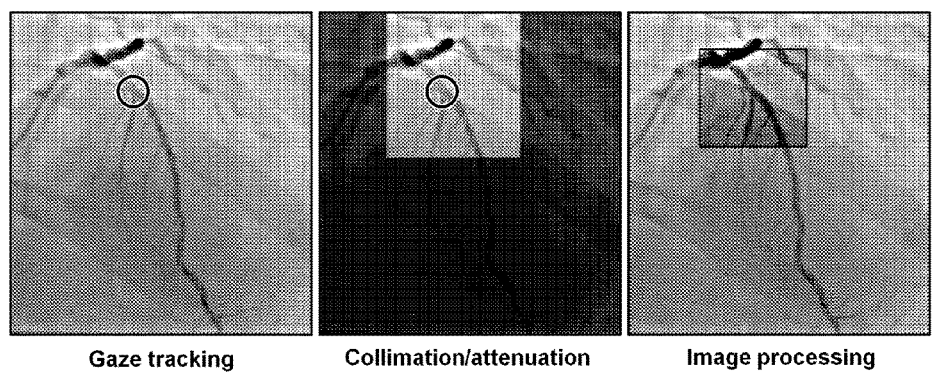
FIG. 6 illustrates a local image processing operation made during a possible application of an embodiment of the method.

In FIG. 6, a local image processing example carried out during the application of the method is illustrated. In this example, the region of interest R is delimited by a circle (illustrated on the left image and on the one of the middle for a better understanding, but optionally displayed on the screen during step 103); the local image processing algorithm of step 403 applies collimation and/or attenuation, as illustrated on the image of the middle and another processing operation restricted to the square area of the right image.

Figure 7:
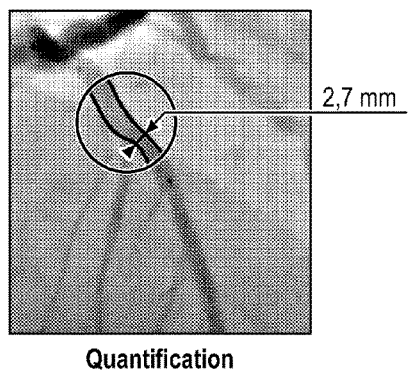
FIG. 7 illustrates a possible display example for quantifying stenosis of a blood vessel according to an embodiment of the method.

In FIG. 7 is also illustrated an example of descriptive information of the region of interest which is displayed during step 106. In this example, it is sought to quantify stenosis of a blood vessel seen by the observer; the displayed pieces of descriptive information may then comprise a double arrow delimiting the narrowest section of the vessel in the area of interest observed by the observer after applying a suitable algorithm for quantifying stenosis, known per se.

The local image processing algorithm may for example consist in an algorithm detecting the presence of surgical instruments in the persistent area ZP, in the case when the practitioner O is operating a patient. Other patterns may also be detected, and other types of algorithms may also be applied after defining the persistent area ZP.

The medical imaging device 1 may comprise, in addition to the screen 2 adapted for displaying medical images according to the method described earlier, a second screen (not shown) displaying a sole portion of the same zoomed medical image IM on the region of interest R.

The medical imaging device 1 may also comprise a motor-driven support, the screen and the camera 3 being mounted mobile on the support and set into motion by the support, for example into rotation. The image processing module 4 may then drive the motor of the support so as to maintain the eyes of the practitioner substantially at the center of the tracking images acquired by camera 3. Further, the screen may be positioned perpendicularly relatively to the axis of the gaze of the practitioner O which gives the possibility of improving the comfort when the practitioner O consults the screen.

Provision may also be made in the device 1 for a light source 6 controlled by the image processing unit 4. The light source may be fixedly oriented towards the practitioner, or else mounted attached to the screen and to the camera when the device 1 comprises the motor driven support 7 as described earlier.

In the case when the analysis step 201 does not determine any pixel of interest PX contemplated on the screen by the practitioner, the light source 6 may be activated. This use of a light source is particularly advantageous in the case when the practitioner operates a patient in the presence of colleagues or auxiliaries localized nearby.

Moreover, the image processing module 4 may be configured for elaborating a mosaic of several elementary medical images to be displayed on the screen 2, and for the analysis step to determine from a tracking image IS at least one elementary medical image IM contemplated by the practitioner, and to determine a region of interest for this elementary medical image IM alone. It is then possible to enhance (with a zoom for example) the image IM relatively to the other images of the mosaic.

Alternatively, several medical images may be simultaneously displayed on respective screens, and the analysis step may determine from a tracking image IS which screen was contemplated by the practitioner, and determine a region of interest for the medical image IM displayed on this contemplated screen.

Moreover in the case when a plurality of medical images IM has been acquired previously by a mobile acquisition device (not shown), a plurality of regions of interest determined by the image processing method described may be combined so as to generate a 3D region of interest.

What is claimed is:

1. An image processing method applied by a medical imaging device comprising at least one camera and at least one display screen on which is displayed a medical image of a patient, the method comprising:
    determining a region of interest within the medical image by:
        arranging the display screen and the camera to simultaneously face a practitioner;
        acquiring with the camera at least one tracking image referencing and/or showing the eyes of the practitioner;
        analyzing the tracking image and localizing, within the medical image, at least one pixel of interest being contemplated by the practitioner based on an orientation of the eyes of the practitioner relative to the display screen;
        processing the medical image to select the region of interest within the medical image based on the localized at least one pixel of interest; and
    wherein the above steps are repeated for a plurality of medical images successively displayed on the display screen, and the method further comprises:
        storing in memory a plurality of regions of interest determined for the plurality of displayed medical images;
        detecting at least one persistent pixel comprised in each region of interest of said plurality; and
        applying a local processing algorithm achieved in at least one following medical image, the realtime processing algorithm being restricted to a portion of the following medical image containing the persistent pixel.

2. The image processing method according to claim 1, further comprising displaying on the display screen a pattern localizing the determined region of interest-in the displayed medical image.

3. The image processing method according claim 2, further comprising determining and displaying descriptive information of the determined region of interest.

4. The image processing method according to claim 1, further comprising adjusting the contrast of at least one portion of the medical image so as to highlight the determined region of interest relatively to the remainder of the displayed medical image.

5. The image processing method according to claim 1, wherein the real time processing algorithm applies detection of surgical instruments in the portions of the medical image.

6. The image processing method according to claim 1, comprising the following steps after acquisition and analysis of a plurality of tracking images:
    determining for each pixel of the medical image, a respective attention coefficient depending on the number of tracking images in which the pixel has crossed the gaze of the practitioner;
    constructing a set of transparent pixels, each pixel in the set corresponding to the respective attention coefficient determined for each pixel of the medical image;
    merging the medical image and the set of transparent pixels into an attention image with which the set of transparent pixels and the medical image may be viewed by transparence through the set of transparent pixels; and
    saving the attention image in a storage unit of the medical imaging device.

7. The image processing method according to claim 1, further comprising activating a light source of the medical imaging device, if the analysis step fails in localizing any pixel of interest contemplated by the practitioner on the screen, from at least one acquired tracking image.

8. The image processing method according to claim 1, further comprising, with the displayed medical image being a mosaic of elementary images, selectively magnifying the elementary medical image in which the pixel of interest is comprised.

9. A medical imaging device comprising:
at least one display screen, at least one camera, and an image processing module comprising a computer directly or indirectly in communication with a memory, wherein the display screen and the camera are arranged to simultaneously face a practitioner, the image processing module configured to:
   localize, within a medical image displayed by the display screen, at least one identified pixel of interest from a tracking image acquired by the camera based on an orientation of the eyes of the practitioner relative to the display screen;
   process the medical image to select a region of interest within the medical image based on the localized at least one identified pixel of interest;
   store in memory a plurality of regions of interest determined for a plurality of displayed medical images;
   detect at least one persistent pixel comprised in each region of interest of said plurality; and
   apply a local processing algorithm achieved in at least one following medical image, the realtime processing algorithm being restricted to a portion of the following medical image containing the persistent pixel.

* * * * *